United States Patent [19]

Shirato et al.

[11] Patent Number: 4,629,561
[45] Date of Patent: Dec. 16, 1986

[54] LIQUID CHROMATOGRAPH WITH FLOW CONTROLLER

[75] Inventors: Kozo Shirato, Omiya; Kazuo Hiraizumi, Narashino; Akio Kaneko, Omiya; Akihiko Nagai, Kawaguchi, all of Japan

[73] Assignee: ERMA Optical Works, Ltd., Tokyo, Japan

[21] Appl. No.: 703,398

[22] Filed: Feb. 20, 1985

[30] Foreign Application Priority Data

Nov. 30, 1984 [JP] Japan ................. 59-254317

[51] Int. Cl.[4] ............................. B01D 15/08
[52] U.S. Cl. .................. 210/198.2; 55/386; 73/61.1 C; 137/501; 422/70
[58] Field of Search .............. 73/61.1 C; 137/501; 210/659, 101, 198.2; 422/70; 55/386

[56] References Cited

U.S. PATENT DOCUMENTS 4,016,074  4/1977  Porter .................. 210/659
4,131,427  12/1978  Karp ................. 73/61.1 C
4,290,776  9/1981  Yamada ............... 210/659

Primary Examiner—Ernest G. Therkorn
Attorney, Agent, or Firm—Watson, Cole, Grindle & Watson

[57] ABSTRACT

A liquid chromatograph includes a solvent tank, a pump, a sample injection element, a column, a detector, conduits for successively interconnecting these elements, and a flow controller which is connected between the pump and the detector and in parallel with the column.

1 Claim, 4 Drawing Figures

LIQUID CHROMATOGRAPH WITH FLOW CONTROLLER

BACKGROUND OF THE INVENTION

This invention relates to a liquid chromatograph, and more particularly to a conventional liquid chromatograph of the type shown in FIG. 4 which includes a solvent tank 1, a pump 2, a sample injection element 3, a column 4, a detector 5, and a recycle cock 6 for recycling solvent leaving the detector 5 back to the detector as a reference solution or exhausting the solvent into a waste tank 7.

In such a conventional liquid chromatograph it is difficult to flow in flowing the solvent at a minutely fixed flow rate and, therefore, it is hard to maintain a high stability of the measured value. This problem becomes revealed particularly when a highly sensitive detector is used or when a volatile solvent such as tetrahydrofuran or the like is used. In this regard, experience has shown that a high stability can be obtained when the solvent flows at a minutely fixed flow rate. At the same time, a greater flow rate of the solvent increases waste consumption of the solvent uneconomically. In addition, the solvent (reference solution) is easily affected by thermal influence in the detector, and a stable baseline cannot be obtained because drift is caused by thermal expansion of the reference solution. Moreover, when a minutely fixed flow rate of the solvent is not maintained, fluctuation of retention time (time until a measured value is reported) prevents accurate measurement and such inconvenience is caused that the measured value cannot be subjected to computer-processing.

OBJECT OF THE INVENTION

It is an object of this invention to provide a liquid chromatograph in which the flow rate of a reference solution (solvent) can be controlled at a minutely fixed flow rate and, as a result, the reference solution (solvent) is much less by thermal influence in the detector, even when using a highly sensitive detector or when using a volatile solvent, resulting in prevention of drift caused by thermal expansion and in maintenance of a stable baseline and, moreover, computer-processing becomes possible as retention time is stabilized to afford accurate measurement.

DETAILED DESCRIPTION OF THE INVENTION

Figure 1:
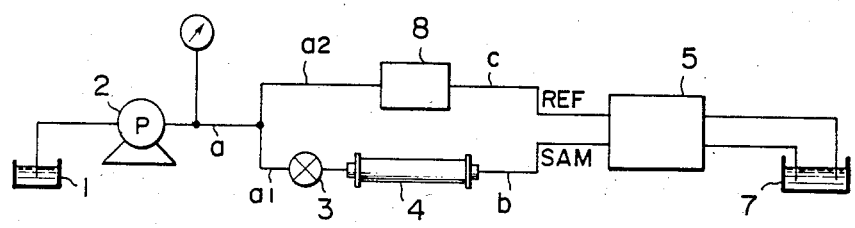
FIG. 1 is a structural diagram illustrating an embodiment of a liquid chromatograph of this invention.

An embodiment of this invention is illustrated based on the structural diagram shown in FIG. 1.

In the drawing, (1) is a solvent tank, (2) is a pump, (3) is a samle injection part, (4) is a column, (8) is a flow controller, (5) is a detector, and (7) is a waste tank, and these are successively connected by conduits.

A pipe (a) on the exhaust side of the pump (2) is branched into two (a1) and (a2) to connect the sample injection part (3) and the column (4) with the one pipe (a1) and the flow controller (8) with the other pipe (a2) and, thus, the column (4) and the flow controller (8) are connected in parallel to each other on the exhaust side of the pump (2). Furthermore, a pipe (b) on the outlet side of the column (4) is connected to the sample inlet of the detector (5) and a pipe (c) on the outlet side of the flow controller (8) is connected to the reference solution inlet of the detector (5).

As far as the detector (5) is concerned, it can be a conventional detector, e.g., a differential refrectometer, an ultraviolet photometer, a fluorescent detector, an electrochemical detector, an ion-exchange detector. These detectors can be used alone or in a proper combination.

Figure 2:
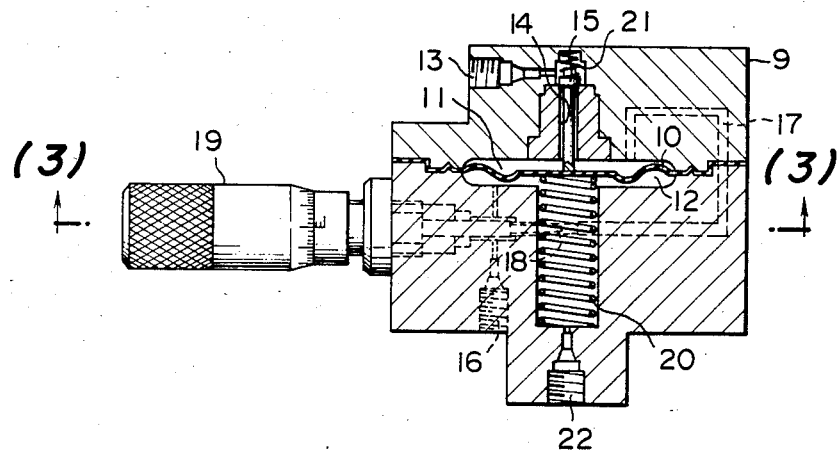
FIG. 2 is a sectional view illustrating an embodiment of a flow controller related to this invention.
Figure 3:
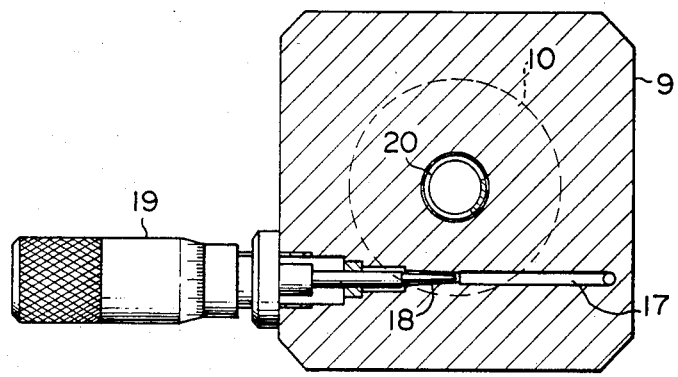
FIG. 3 is a sectional view taken substantially on line (3)—(3) of FIG. 2.
Figure 4:
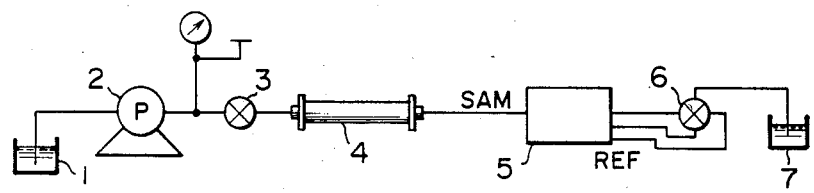
FIG. 4 is a structural diagram illustrating a conventional liquid chromatograph.

The flow controller (8), which is a main component material of this invention, is illustrated in FIGS. 2 and 3. This flow controller (8) is composed of an upper chamber (11) and a lower chamber (12) comparted by a diaphragm (10), which are formed in a unit (9), an inlet passage (14) to connect the upper chamber (11) with a solvent inlet (13), an adjustment valve (15) positioned inside the passage (14), one end of which is fixed on the noted diaphragm (10), an adjustment passage (17) to connect the upper chamber (11) with the lower chamber (12) and to connect with a solvent outlet (16), a needle valve (18) positioned in a face of the inside of this adjustment passage (17), a micrometer head (19) to adjust the needle valve (18), and a compression spring (20) to compress the noted diaphragm (10) from the lower chamber (12) side. Namely, the upper chamber (11) and the lower chamber (12), comparted by the diaphragm (10), are formed in the unit (9) and, furthermore, the unit is provided with the passage (14) to connect the upper chamber (11) with the solvent inlet (13) and the adjustment passage (17) to connect the upper chamber (11) and the lower chamber (12) and to connect with the solvent outlet (16). The diaphragm (10) is in the form of a wave plate in order to widen the surface area as much as possible, and the adjustment vale (15) is positioned inside the passage (14) leading to the noted upper chamber (11). This adjustment valve (15) is provided to adjust the flow rate of the solvent entering from the solvent inlet (13), one end of the valve being connected to the diaphragm (10) to operate together with the diaphragm (10) and the other end being compressed by the spring (21) in order not to operate inadvertently. The needle valve (18) is positioned in face of the inside of the adjustment passage (17) to connect the noted upper chamber (11) with the lower chamber (12) and the solvent outlet (16). This needle valve (18) is provided to adjust the flow rate out of the solvent outlet (16) of the fluid coming through the adjustment passage (17), and the opening degree of the valve is adjusted by the micrometer head (19) attached to the unit (9). The micrometer head (19) has a similar mechanism to those of micrometers, moving the needle valve (18) minutely. The inside of the noted lower chamber (12) is provided with the compression spring (20) to compress the diaphragm (10) always toward the upper chamber (11) side. In the drawing, (22) is a drain for use in exchange of the solvent and the like.

To the solvent inlet (13) of the flow controller (8) thus composed is connected the other pipe (a2) of the exhaust side pipe (a) of the pump (2), and to the solvent outlet (16) is connected the pipe (c) connecting to the reference solution inlet of the detector (5).

In this way, the solvent exhausted from the pump (2) is branched, through the exhaust side pipe (a), into the pipe (a2) of the flow controller (8) side and the pipe (a1) of the column (4) side, and a sample is added to the solvent of the column (4) side from the sample injection part (3) and separated by the column (4) and provided to the sample solution inlet of the detector. On the other hand, the solvent branched to the flow controller (8) side enters in the upper chamber (11) from the inlet (13) through the passage (14) and flows from the upper chamber (11) through the passage (17) and divided a part entering into the lower chamber (12) through the needle valve (18) and a part leading to the outlet (16). The compressive force of the compression spring (20) and the pressure of the outlet (16) side are added to the lower chamber (12), and the pressure of the solvent entering into the upper chamber (11) is adjusted so as to maintain the balance with these pressures. In this way, since the pressure balance between the upper chamber (11) and the lower chamber (12) is maintained and the difference before and behind the needle valve (18) is always fixed, the flow rate of the solvent is adjusted minutely only by the opening degree of the needle valve (18), or adjustment by the micrometer head (19), and provided to the reference solution inlet of the detector (5) without being affected by any pressure fluctuation of the solvent entering from the inlet (13) at all. The flow controller (8) thus composed can afford a high stability in a short time and pulsation of the pump (2) can be also controlled by widening the surface area of the diaphragm (10).

As is apparent from the description so far, according to the liquid chromatograph of this invention, the flow rate of the reference solution side can be controlled at a minutely fixed flow rate and, therefore, a high stability can be obtained even in the case of using a volatile solvent or using a highly sensitive detector. Namely, since the flow rate of the reference solution can be controlled at a minutely fixed flow rate, the solvent (reference solution) becomes hard to be affected by thermal influence in the detector, resulting in prevention of drift caused by thermal expansion and in maintenance of a stable baseline and, furthermore, computer-processing becomes possible as retention time is stabilized to afford accurate measurement.

What is claimed is:

1. In a liquid chromatograph which includes a solvent tank, a pump, a sample injection element, a column, a detector, and conduits for successively connecting said solvent tank, said sample injection element, said column and said detector together, said detector including a sample solution inlet and a reference solution inlet and said column being connected between said pump and said sample solution inlet of said detector, the improvement wherein said liquid chromatograph includes a flow controller connected in parallel with said column between said pump and said reference solution inlet of said detector, said flow controller comprising a fluid inlet, a fluid outlet, an internal chamber, a diaphragm in said internal chamber dividing said internal chamber into an upper chamber and a lower chamber, an inlet passage connecting said upper chamber with said fluid inlet, an adjustment valve positioned in said inlet passage and connected to said diaphragm, an adjustment passage connecting said upper chamber with both said lower chamber and said fluid outlet, a needle valve capable of closing off said adjustment passage, a micrometer head to adjust said needle valve, and a compression spring positioned inside said lower chamber to bias said diaphragm toward the upper chamber.

* * * * *